US 6,617,407 B1

United States Patent
Klosin (10) Patent No.: US 6,617,407 B1
(45) Date of Patent: Sep. 9, 2003

(54) BIS(N,N-DIHYDROCARBYLAMINO)-SUBSTITUTED CYCLOPENTADIENES AND METAL COMPLEXES THEREOF

(75) Inventor: Jerzy Klosin, Midland, MI (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/936,239

(22) PCT Filed: Mar. 17, 2000

(86) PCT No.: PCT/US00/07373

§ 371 (c)(1),
(2), (4) Date: Sep. 7, 2001

(87) PCT Pub. No.: WO00/66596

PCT Pub. Date: Nov. 9, 2000

Related U.S. Application Data (60) Provisional application No. 60/131,547, filed on Apr. 29, 1999.

(51) Int. Cl.⁷ .................................................. C08F 4/64
(52) U.S. Cl. .................. 526/172; 526/133; 526/134; 526/160; 526/161; 502/155; 556/53
(58) Field of Search .................. 556/53; 526/172, 526/160, 161, 133, 134; 502/155

(56) References Cited

U.S. PATENT DOCUMENTS

| 5,055,438 A | 10/1991 | Canich |
| 5,057,475 A | 10/1991 | Canich et al. |
| 5,064,802 A | 11/1991 | Stevens et al. |
| 5,096,867 A | 3/1992 | Canich |
| 5,132,380 A | 7/1992 | Stevens et al. |
| 5,621,126 A | 4/1997 | Canich et al. |
| 5,703,187 A | 12/1997 | Timmers |

FOREIGN PATENT DOCUMENTS

| EP | 0 416 815 A2 | 3/1991 |
| EP | 0 416 815 B1 | 3/1991 |
| EP | 0 514 828 B1 | 5/1992 |
| EP | 0 577 581 B1 | 1/1994 |
| JP | 06228552 | 2/1993 |
| WO | WO 95/00526 | 1/1995 |
| WO | WO 95/07942 | 3/1995 |
| WO | WO 96/13529 | 5/1996 |
| WO | WO 98/06727 | 2/1998 |
| WO | WO 98/06728 | 2/1998 |

OTHER PUBLICATIONS

J. Organometallic Chem. 1996, 520, 63–68 E. Barsties, S. Schaible, M. H. Prosenc, U. Rief, W. Roll, O. Weyland, B. Dorerer, and H. H. Brintzinger.

*Primary Examiner*—Caixia Lu (57) ABSTRACT

This invention relates to bis(N,N-dihydrocarbylamino)-substituted derivatives of cyclopentadienes (Cp) and metal complexes thereof which find utility as olefin polymerization catalyst components.

6 Claims, 1 Drawing Sheet

FIG. 1

BIS(N,N-DIHYDROCARBYLAMINO)-SUBSTITUTED CYCLOPENTADIENES AND METAL COMPLEXES THEREOF

This application claims the benefit of Provisional application Ser. No. 60/131,547, filed Apr. 29, 1999.

FIELD OF THE INVENTION

This invention relates to bis(N,N-dihydrocarbylamino)-substituted derivatives of cyclopentadienes (Cp) and metal complexes thereof which find utility as olefin polymerization catalyst components.

BACKGROUND

Constrained geometry complexes (CGC) and methods for their preparation are disclosed in U.S. Pat. Nos. 5,703,187, 5,064,802, 5,055,438, 5,057,475, 5,096,867, 5,064,802, 5,132,380, as well as EP-A-514,828, WO 95/00526, and elsewhere. EP-A-577,581 discloses unsymmetrical bis-Cp metallocenes containing a fluorenyl ligand with heteroatom substituents.

E. Barsties; S. Schaible; M.-H. Prosenc; U. Rief; W. Roll; O. Weyland; B. Dorerer; H.-H. Brintzinger, *J. Organometallic Chem.* 1996, 520, 63–68, and H. Plenio; D. Birth, *J. Organometallic Chem.* 1996, 519, 269–272 disclose non-bridged and Si-bridged ansa bis-indenyl complexes in which the 5 membered ring of the indenyl group is substituted with a dimethylamino substituent. The complexes were disclosed as useful components of catalysts for use in the formation of polyethylene and isotactic polypropylene.

Disclosure of random heteroatom substitution in mono-Cp metallocenes is found in EP-A-416,815, WO 95/07942, WO 96/13529, and U.S. Pat. Nos. 5,096,867 and 5,621,126. Specific heteroatom substitution of the 3- and 2-position of indenyl complexes of group 4 metals was disclosed in WO98/06727 and WO/98/06728 respectively. The foregoing specifically substituted metal complexes have produced improved catalyst results, however, problems still remain with catalyst efficiency and deactivation of the catalyst under high temperature polymerization conditions. It would be advantageous to be able to produce polyolefins with higher molecular weights. It would also be advantageous to be able to improve other physical characteristics of the polymers produced by altering the substitution around the cyclopentadienyl group of the metallocene complexes used in olefin polymerization catalyst systems.

SUMMARY OF THE INVENTION

The present invention provides novel bis(N,N-dihydrocarbylamino)-substituted derivatives of cyclopentadienes corresponding to the formula:

IA

IB

IC

IIA

IIB   or

IIC where,
$R^B$ and $R^C$ independently each occurrence are hydrocarbyl, hydrocarbylsilyl, halo-substituted hydrocarbyl, hydrocarbyloxy-substituted hydrocarbyl, di(hydrocarbyl)amino-substituted hydrocarbyl, hydrocarbylsilylhydrocarbyl, hydrocarbadiylamino, di(hydrocarbyl)amino, or hydrocarbyloxy, each $R^B$ and $R^C$ having from 1 to 80 atoms not counting hydrogen, and optionally being substituted with one or more groups which independently each occurrence are hydrocarbyloxy, hydrocarbylsiloxy, hydrocarbylsilylamino, di(hydrocarbylsilyl)amino, hydrocarbadiylamino, di(hydrocarbyl)amino, di(hydrocarbyl)phosphino, hydrocarbylsulfido, hydrocarbyl, hydrocarbyisilyl, hydrocarbylsilylhydrocarbyl, halo-substituted hydrocarbyl, hydrocarbyloxy-substituted hydrocarbyl, or hydrocarbylamino-substituted hydrocarbyl, said group having from 1 to 20 atoms not counting hydrogen, or two $R^B$ or two $R^C$ groups are covalently linked to form one or more fused rings; and $R^A$ independently each occurrence is hydrogen, hydrocarbyl, halo-substituted hydrocarbyl, hydrocarbyloxy-substituted hydrocarbyl, dihydrocarbylamino-substituted hydrocarbyl, hydrocarbadiylamino, hydrocarbylsilyl, hydrocarbylsilylhydrocarbyl, or one of the forgoing groups that is substituted with one or more hydrocarbyloxy, hydrocarbylsiloxy, hydrocarbylsilylamino, di(hydrocarbylsilyl)amino, hydrocarbadiylamino, di(hydrocarbyl)amino, di(hydrocarbyl)phosphino, hydrocarbylsulfido, hydrocarbyl, halo-substituted hydrocarbyl, hydrocarbyloxy-substituted hydrocarbyl, hydrocarbylamino-substituted hydrocarbyl, hydrocarbylsilyl or hydrocarbylsilylhydrocarbyl groups having from 1 to 20 nonhydrogen atoms.

The present invention further provides metal complexes corresponding to the formula:

wherein
M is a metal from one of Groups 3 to 13 of the Periodic Table of the Elements, the lanthanides or actinides, which is in the +2, +3 or +4 formal oxidation state, Z is a divalent moiety comprising boron, or a member of Group 14 of the Periodic Table of the Elements, and also comprising nitrogen, phosphorus, sulfur or oxygen;

X is an anionic or dianionic ligand group having up to 60 atoms exclusive of the class of ligands that are cyclic, delocalized, π-bound ligand groups;

X' independently each occurrence is a neutral Lewis base ligand having up to 20 atoms;

p is zero, 1 or 2, and is two less than the formal oxidation state of M, when X is an anionic ligand; when X is a dianionic ligand group, p is 1; and q is zero, 1 or 2.

Complexes III and IV are the predominant reaction products of the present invention. Complexes IIIA and IVA are less favored due to steric effects and generally are prepared in minor amounts only. The above metal complexes may exist as isolated crystals optionally in pure form or as a mixture (including as a mixture with other complexes), in the form of a solvated adduct, optionally in a solvent, especially an organic liquid, as well as in the form of a dimer or chelated derivative thereof. Suitable chelating agents include organic compounds, preferably Lewis bases, especially trihydrocarbylamines, trihydrocarbylphosphines, halogenated derivatives thereof, or ethers.

Also, according to the present invention, there is provided a catalyst composition for olefin polymerization prepared from catalyst system components comprising:

(A) a metal complex of one or more of the aforementioned Formulae III, IIIA, IV, or IVA; and (B) an activating cocatalyst wherein the molar ratio of (A) to (B) is from 1:10,000 to 100:1.

Another embodiment of this invention is a catalyst composition for olefin polymerization prepared from catalyst system components comprising:

(A) a metal complex of one or more of the aforementioned metal complexes of Formulae III, IIIA, IV, or IVA; and (B) an activating cocatalyst, wherein the molar ratio of (A) to (B) is from 1:10,000 to 100:1, and the metal complex is in the form of a cation.

Further according to the present invention there is provided a process for the polymerization of olefins comprising contacting one or more $C_{2-20}$ α-olefins under polymerization conditions with one of the aforementioned catalyst compositions.

A preferred process of this invention is a high temperature solution polymerization process for the polymerization of olefins comprising contacting one or more $C_{2-20}$ α-olefins under polymerization conditions with one of the aforementioned catalyst compositions at a temperature from 100° C. to 250° C.

Within the scope of this invention are the polyolefin products produced by the aforementioned processes. Preferred products have long chain branching and reverse molecular architecture.

The present catalysts and processes result in the highly efficient production of high molecular weight olefin polymers over a wide range of polymerization conditions, and especially at elevated temperatures. They are especially useful for the solution or bulk polymerization of ethylene/propylene (EP polymers), ethylene/octene (EO polymers), ethylene/styrene (ES polymers), propylene and ethylene/propylene/diene (EPDM polymers) wherein the diene is ethylidenenorbornene, 1,4-hexadiene or similar nonconjugated diene. The use of elevated temperatures dramatically increases the productivity of such processes due to the fact that increased polymer solubility at elevated temperatures allows the use of increased conversions (higher concentration of polymer product) without exceeding solution viscosity limitations of the polymerization equipment as well as reduced energy costs needed to devolatilize the reaction product.

The catalyst compositions of this invention may also include a support material and may be used in olefin polymerization processes in a slurry or in the gas phase. The catalyst may be prepolymerized with one or more olefin monomers in situ in a polymerization reactor or in a separate process with intermediate recovery of the prepolymerized catalyst prior to the primary polymerization process.

DETAILED DESCRIPTION

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups. The full teachings of any patent, patent application, provisional application, or publication referred to herein are hereby incorporated by reference. The term "reverse molecular architecture" as used herein refers to a copolymer of two or more olefins wherein higher molecular weight fractions of the polymer contain increased content of the higher molecular weight comonomer. The terms "cyclopentadiene", "Cp", or "cyclopentadienyl", when used for purposes of the present invention refers solely to single ring compounds and ligands derived therefrom, and specifically excludes multiple ring compounds such as indene, fluorene, partially hydrogenated derivatives thereof, and ligand derivatives thereof.

The novel bis(N,N-dihydrocarbylamino)-substituted derivatives of cyclopentadienes of the invention are prepared from starting materials known in the literature, in particular 1,3-cyclopentadiones, 1,2-cyclopentadiones, substituted 1,3-cyclopentadiones and substituted 1,2-cyclopentadiones which are reacted with titanium tetraamides. The formation of the bis(N,N-dihydrocarbylamino)-substituted derivatives of cyclopentadienes is readily accomplished by combining the starting cyclopentadione with the titanium tetraamide in an organic solvent and recovering the product.

Preferred bis(N,N-dihydrocarbylamino)-substituted derivatives of cyclopentadienes of the present invention correspond to the formulas I and II, wherein $R^B$ and $R^C$ are hydrocarbyl, hydrocarbyloxy-substituted hydrocarbyl, N,N-dihydrocarbylamino and hydrocarbadiylamino-substituted hydrocarbyl radicals of 1–20 carbon atoms and cyclic radicals in which two $R^B$ or two $R^C$ radicals combine to form a ring strcture and wherein $R^A$ is hydrogen, or a hydrocarbyl, halo-substituted hydrocarbyl, hydrocarbyloxy-substituted hydrocarbyl, or N,N-dihydrocarbylamino-substituted hydrocarbyl radical containing from 1–20 carbon atoms.

Olefins, as used herein, are $C_{2-20}$ aliphatic or aromatic compounds containing vinylic unsaturation, as well as cyclic compounds such as cyclobutene, cyclopentene, and norbornene, including norbornene substituted in the 5- and 6-positions with $C_{1-20}$ hydrocarbyl groups. Also included are mixtures of such olefins as well as mixtures of such olefins with $C_{4-40}$ diolefin compounds. Examples of the latter compounds include ethylidene norbornene, 1,4-hexadiene, norbornadiene, and the like. The catalysts and processes herein are especially suited for use in preparation of ethylene/1-butene-, ethylene/1-hexene-, ethylene/styrene-, ethylene/propylene-, ethylene/1-pentene-, ethylene/4-methyl-1-pentene- and ethylene/1-octene-copolymers as well as terpolymers of ethylene, propylene and a nonconjugated diene, such as, for example, EPDM terpolymers.

Preferred coordination complexes according to the present invention are complexes corresponding to the formulas III and IV, wherein $R^B$ and $R^C$ are hydrocarbyl, hydrocarbyloxy-substituted hydrocarbyl, N,N-dihydrocarbadiamino and hydrocarbadiylamino-substituted hydrocarbyl radicals of 1–20 carbon atoms and cyclic radicals in which two $R^B$ or two $R^C$ radicals combine to form a ring structure and wherein $R^A$ is hydrogen, or a hydrocarbyl, halo-substituted hydrocarbyl, hydrocarbyloxy-substituted hydrocarbyl, N,N-dihydrocarbyamino-substituted hydrocarbyl, or hydrocarbadiylamino-substituted hydrocarbyl radical containing from 1–20 carbon atoms, the remaining moieties of the complex being as previously identified.

Preferred X' groups in the bis(N,N-dihydrocarbylamino)-substituted cyclopentadiene containing metal complexes of the present invention are carbon monoxide; phosphines, especially trimethylphosphine, triethylphosphine, triphenylphosphine and bis(1,2-dimethylphosphino)ethane; $P(OR^D)_3$, wherein $R^D$ is hydrocarbyl, silyl or a combination thereof; ethers, especially tetrahydrofuran; amines, especially pyridine, bipyridine, tetramethylethylenediamine (TMEDA), and triethylamine; olefins; and conjugated dienes having from 4 to 40 carbon atoms. Complexes including the latter X' groups include those wherein the metal is in the +2 formal oxidation state.

Highly preferred are the metal complexes where —Z— is —(Z*—Y)—, with Z* bonded to the bis(N,N-dihydrocarbylamino)-substituted cyclopentadienyl group and Y bonded to M, and Y is —O—, —S—, —NR*—, —PR*—;

Z* is $SiR^*_2$, $CR^*_2$, $SiR^*_2SiR^*_2$, $CR^*_2CR^*_2$, $CR^*=CR^*$, $CR^*_2SiR^*_2$, $CR^*_2SiR^*_2CR^*_2$, $SiR^*_2CR^*_2SiR^*_2$, $CR^*_2CR^*_2SiR^*_2$, $CR^*_2CR^*_2CR^*_2$, B—NR*$_2$ or GeR*$_2$; and R* independently each occurrence is hydrogen, or a member selected from hydrocarbyl, hydrocarbyloxy, sily, halogenated alkyl, halogenated aryl, and combinations thereof, said R* having up to 20 nonhydrogen atoms, and optionally, two R* groups from Z (when R* is not hydrogen), or an group from Z group from Y form a ring system;

where p is 2, q is zero, M is in the +4 formal oxidation state, and X is independently each occurrence methyl, benzyl, trimethylsilylmethyl, allyl, pyrollyl or two X groups together are butane-1,4-diyl, 2-butene-1,4-diyl, 2,3-dimethyl-2-butene-1,4-diyl, 2-methyl-2-butene-1,4-diyl, or xylenediyl.

Also highly preferred are metal complexes where —Z— is —(Z*—Y)—, with Z* bonded to the bis(N,N-dihydrocarbylamino)-substituted cyclopentadienyl group and Y bonded to M, and Y is —O—, —S—, —NR*—, —PR*—;

Z* is $SiR^*_2$, $CR^*_2$, $SiR^*_2SiR^*_2$, $CR^*_2CR^*_2$, $CR^*=CR^*$, $CR^*_2SiR^*_2$, $CR^*_2SiR^*_2CR^*_2$, $SiR^*_2CR^*_2SiR^*_2$, $CR^*_2CR^*_2SiR^*_2$, $CR^*_2CR^*_2CR^*_2$, B—NR*$_2$ or GeR*$_2$; and R* independently each occurrence is hydrogen, or a member selected from hydrocarbyl, hydrocarbyloxy, silyl, halogenated alkyl, halogenated aryl, and combinations thereof, said R* having up to 20 atoms not counting hydrogen, and optionally, two R* groups from Z (when R* is not hydrogen), or an R* group from Z and an R* group from Y form a ring system;

where p is 1, q is zero, M is in the +3 formal oxidation state, and X is 2-(N,N-dimethyl)aminobenzyl, 2-(N,N-dimethylaminomethyl)phenyl, allyl, methallyl, trimethylsilylallyl.

Also highly preferred are metal complexes where —Z— is —(Z*—Y)—, with Z* bonded to the bis(N,N-dihydrocarbylamino)-substituted cyclopentadienyl group and Y bonded to M, and Y is —O—, —S—, —NR*—, —PR*—;

Z* is $SiR^*_2$, $CR^*_2$, $SiR^*_2SiR^*_2$, $CR^*_2CR^*_2$, $CR^*=CR^*$, $CR^*_2SiR^*_2$, $CR^*_2SiR^*_2CR^*_2$, $SiR^*_2CR^*_2SiR^*_2$, $CR^*_2CR^*_2SiR^*_2$, $CR^*_2CR^*_2CR^*_2$, or GeR*$_2$; and R* independently each occurrence is hydrogen, or a member selected from hydrocarbyl, hydrocarbyloxy, silyl, halogenated alkyl, halogenated aryl, and combinations thereof, said R* having up to 20 nonhydrogen atoms, and optionally, two R* groups from Z (when R* is not hydrogen), or an R* group from Z and an R* group from Y form a ring system;

when p is 0, q is 1, M is in the +2 formal oxidation state, and X' is 1,4-diphenyl-1,3-butadiene, 1,3-pentadiene or 2,4-hexadiene.

A variety of metals can be used in the preparation of the metal complexes of this invention, desirably a metal from one of Groups 3 to 13 of the Periodic Table of the Elements, the lanthanides or actinides, which is in the +2, +3 or +4 formal oxidation state, more desirably a metal from one of Groups 3 to 5. Preferred are those metal complexes where M is a metal from Group 4, (Ti, Zr or Hf), with Ti and Zr being most highly preferred.

In another aspect of this invention it is preferred that Y is —NR*, with the more preferred —NR* being those where R* is a group having a primary or secondary carbon atom bonded to N. Highly preferred are compounds where R* is cyclohexyl or isopropyl.

The metal complexes of the present invention preferably correspond to the formula:

IIIB wherein —N($R^B$)$_2$ and —N($R^C$)$_2$ are independently N,N-dimethylamino or pyrrolidino, $R^A$ independently each occurrence is methyl or hydrogen, M is titanium, and X is chloride or methyl.

Illustrative metal complexes of the present invention include:

dichloro[N-(1,1-dimethylethyl)-1-[(1,2,3,4,5-eta)-2,4-bis(N,N-dimethylamino)-2,4-cyclopentadien-1-yl]-1,1-dimethylsilanaminato(2-)-kappaN]-titanium dichloro[N-(1,1-dimethylethyl)-1-[(1,2,3,4,5-eta)-2,3-bis(N,N-dimethylamino)-2,4-cyclopentadien-1-yl]-1,1-dimethylsilanaminato(2-)-kappaN]-titanium dichloro[N-(1,1-dimethylethyl)-1-[(1,2,3,4,5-eta)-2,5-bis(N,N-dimethylamino)-2,4-cyclopentadien-1-yl]-1,1-dimethylsilanaminato(2-)-kappaN]-titanium dichloro[N-(1,1-dimethylethyl)-1-[(1,2,3,4,5-eta)-3,4-bis(N,N-dimethylamino)-2,4-cyclopentadien-1-yl]-1,1-dimethylsilanaminato(2-)-kappaN]-titanium

[N-(1,1-dimethylethyl)-1-[(1,2,3,4,5-eta)-2,4-bis(N,N-dimethylamino)-2,4-cyclopentadien-1-yl]-1,1-dimethylsilanaminato(2-)-kappaN][(2,3,4,5-eta)-2,4-hexadiene]-titanium(II)

[N-(1,1-dimethylethyl)-1-[(1,2,3,4,5-eta)-2,3-bis(N,N-dimethylamino)-2,4-cyclopentadien-1-yl]-1,1-dimethylsilanaminato(2-)-kappaN][(2,3,4,5-eta)-2,4-hexadiene]-titanium(II)

[N-(1,1-dimethylethyl)-1-[(1,2,3,4,5-eta)-2,5-di-1-bis(N,N-dimethylamino)-2,4-cyclopentadien-1-yl]-1,1-dimethylsilanaminato(2-)-kappaN][(2,3,4,5-eta)-2,4-hexadiene]-titanium(II)

[N-(1,1-dimethylethyl)-1-[(1,2,3,4,5-eta)-3,4-di-1-bis(N,N-dimethylamino)-2,4-cyclopentadien-1-yl]-1,1-dimethylsilanaminato(2-)-kappaN][(2,3,4,5-eta)-2,4-hexadiene]-titanium(II)

dimethyl[N-(1,1-dimethylethyl)-1-[(1,2,3,4,5-eta)-2,4-bis(N,N-dimethylamino)-2,4-cyclopentadien-1-yl]-1,1-dimethylsilanaminato(2-)-kappaN]-titanium dimethyl[N-(1,1-dimethylethyl)-1-[(1,2,3,4,5-eta)-2,3-bis(N,N-dimethylamino)-2,4-cyclopentadien-1-yl]-1,1-dimethylsilanaminato(2-)-kappaN]-titanium dimethyl[N-(1,1-dimethylethyl)-1-[(1,2,3,4,5-eta)-2,5-bis(N,N-dimethylamino)-2,4-cyclopentadien-1-yl]-1,1-dimethylsilanaminato(2-)-kappaN]-titanium dimethyl[N-(1,1-dimethylethyl)-1-[(1,2,3,4,5-eta)-3,4-bis(N,N-dimethylamino)-2,4-cyclopentadien-1-yl]-1,1-dimethylsilanaminato(2-)-kappaN]-titanium dichloro[(1,1-dimethylethyl)[[(1,2,3,4,5-eta)-2,4-bis(N,N-dimethylamino)-2,4-cyclopentadien-1-yl]dimethylsilyl]phosphido(2-)-kappaP]-titanium

[(1,1-dimethylethyl)[[(1,2,3,4,5-eta)-2,4-bis(N,N-dimethylamino)-2,4-cyclopentadien-1-yl]dimethylsilyl]phosphido(2-)-kappaP][(2,3,4,5-eta)-2,4-hexadiene]-titanium(II)

dimethyl[(1,1-dimethylethyl)[[(1,2,3,4,5-eta)-2,4-bis(N,N-dimethylamino)-2,4-cyclopentadien-1-yl]dimethylsilyl]phosphido(2-)-kappaP]-titanium dichloro[(1,1-dimethylethyl)[[(1,2,3,4,5-eta)-2,4-bis(N,N-dimethylamino)-2,4-cyclopentadien-1-yl]dimethylsilyl]phosphido(2-)-kappaP]di(4-methylphenyl)-titanium dichloro[N-(1,1-dimethylethyl)-1-[(1,2,3,4,5-eta)-2,4-bis(N,N-dimethylamino)-2,4-cyclopentadien-1-yl]-1,1-dimethoxygermanaminato(2-)-kappaN]-titanium dimethyl[N-(1,1-dimethylethyl)-1-[(1,2,3,4,5-eta)-2,4-bis(N,N-dimethylamino)-2,4-cyclopentadien-1-yl]-1,1-dimethoxygermanaminato(2-)-kappaN]-titanium dichloro[N-(1,1-dimethylethyl)-1-[(1,2,3,4,5-eta)-2,5-bis(N,N-dimethylamino)-2,4-cyclopentadien-1-yl]-1,1-dimethoxygermanaminato(2-)-kappaN]-titanium dichloro[N'-(1,1-dimethylethyl)-1-[(1,2,3,4,5-eta)-2,4-bis(N,N-dimethylamino)-2,4-cyclopentadien-1-yl]-N,N-bis(1-methylethyl)boranediaminato(2-)-kappaN]-titanium

[N'-(1,1-dimethylethyl)-1-[(1,2,3,4,5-eta)-2,4bis(N,N-dimethylamino)-2,4-cyclopentadien-1-yl]-N,N-bis(1-methylethyl)boranediaminato(2-)-kappaN'][(2,3,4,5-eta)-2,4-hexadiene]-titanium(II)

dimethyl[N'-(1,1-dimethylethyl)-1-[(1,2,3,4,5eta)-2,4-bis(N,N-dimethylamino)-2,4-cyclopentadien-1-yl]-N,N-bis(1-methylethyl)boranediaminato(2-)-kappaN]-titanium dichloro[N-(1,1-dimethylethyl)-1-[(1,2,3,4,5-eta)-2,4-di-1-pyrrolidino-2,4-cyclopentadien-1-yl]-1,1-dimethylsilanaminato(2-)-kappaN]-titanium dichloro[N-(1,1-dimethylethyl)-1-[(1,2,3,4,5-eta)-2,3-di-1-pyrrolidino-2,4-cyclopentadien-1-yl]-1,1-dimethylsilanaminato(2-)-kappaN]-titanium dichloro[N-(1,1-dimethylethyl)-1-[(1,2,3,4,5-eta)-2,5-di-1-pyrrolidino-2,4-cyclopentadien-1-yl]-1,1-dimethylsilanaminato(2-)-kappaN]-titanium dichloro[N-(1,1-dimethylethyl)-1-[(1,2,3,4,5-eta)-3,4-di-1-pyrrolidino-2,4-cyclopentadien-1-yl]-1,1-dimethylsilanaminato(2-)-kappaN]-titanium

[N-(1,1-dimethylethyl)-1-[(1,2,3,4,5-eta)-2,4-di-1-pyrrolidino-2,4-cyclopentadien-1-yl]-1,1-dimethylsilanaminato(2-)-kappaN][(2,3,4,5-eta)-2,4-hexadiene]-titanium(II)

[N-(1,1-dimethylethyl)-1-[(1,2,3,4,5-eta)-2,3-di-1-pyrrolidino-2,4-cyclopentadien-1-yl]-1,1-dimethylsilanaminato(2-)-kappaN][(2,3,4,5-eta)-2,4-hexadiene]-titanium(II)

[N-(1,1-dimethylethyl)-1-[(1,2,3,4,5-eta)-2,5-di-1-pyrrolidino-2,4-cyclopentadien-1-yl]-1,1-dimethylsilanaminato(2-)-kappaN][(2,3,4,5-eta)-2,4-hexadiene]-titanium(II)

[N-(1,1-dimethylethyl)-1-[(1,2,3,4,5-eta)-3,4-di-1-pyrrolidino-2,4-cyclopentadien-1-yl]-1,1-dimethylsilanaminato(2-)-kappaN][(2,3,4,5-eta)-2,4-hexadiene]-titanium(II)

dimethyl[N-(1,1-dimethylethyl)-1-[(1,2,3,4,5-eta)-2,4-di-1-pyrrolidino-2,4-cyclopentadien-1-yl]-1,1-dimethylsilanaminato(2-)-kappaN]-titanium dimethyl[N-(1,1-dimethylethyl)-1-[(1,2,3,4,5-eta)-2,3-di-1-pyrrolidino-2,4-cyclopentadien-1-yl]-1,1-dimethylsilanaminato(2-)-kappaN]-titanium dimethyl[N-(1,1-dimethylethyl)-1-[(1,2,3,4,5-eta)-2,5-di-1-pyrrolidino-2,4-cyclopentadien-1-yl]-1,1-dimethylsilanaminato(2-)-kappaN]-titanium dimethyl[N-(1,1-dimethylethyl)-1-[(1,2,3,4,5-eta)-3,4-di-1-pyrrolidino-2,4-cyclopentadien-1-yl]-1,1-dimethylsilanaminato(2-)-kappaN]-titanium dichloro[(1,1-dimethylethyl)[[(1,2,3,4,5-eta)-2,4-di-1-pyrrolidino-2,4-cyclopentadien-1-yl]dimethylsilyl]phosphido(2-)-kappaP]-titanium

[(1,1-dimethylethyl)[[(1,2,3,4,5-eta)-2,4-di-1-pyrrolidino-2,4-cyclopentadien-1-yl]dimethylsilyl]phosphido(2-)-kappaP][(2,3,4,5-eta)-2,4-hexadiene]-titanium(II)

dimethyl[(1,1-dimethylethyl)[[(1,2,3,4,5-eta)-2,4-di-1-pyrrolidino-2,4-cyclopentadien-1-yl]dimethylsilyl]phosphido(2-)-kappaP]-titanium dichloro[(1,1-dimethylethyl)[[(1,2,3,4,5-eta)-2,4-di-1-pyrrolidino-2,4-cyclopentadien-1-yl]dimethylsilyl]phosphido(2-)-kappaP]di(4-methylphenyl)-titanium dichloro[N-(1,1-dimethylethyl)-1-[(1,2,3,4,5-eta)-2,4-di-1-pyrrolidino-2,4-cyclopentadien-1-yl]-1,1-dimethoxygermanaminato(2-)-kappaN]-titanium dimethyl[N-(1,1-dimethylethyl)-1-[(1,2,3,4,5-eta)-2,4-di-1-pyrrolidino-2,4-cyclopentadien-1-yl]-1,1-dimethoxygermanaminato(2-)-kappaN]-titanium dichloro[N-(1,1-dimethylethyl)-1-[(1,2,3,4,5-eta)-2,5-di-1-pyrrolidino-2,4-cyclopentadien-1-yl]-1,1-dimethoxygermanaminato(2-)-kappaN]-titanium dichloro[N'-(1,1-dimethylethyl)-1-[(1,2,3,4,5-eta)-2,4-di-1-pyrrolidino-2,4-cyclopentadien-1-yl]-N,N-bis(1-methylethyl)boranediaminato(2-)-kappaN']-titanium

[N'-(1,1-dimethylethyl)-1-[(1,2,3,4,5-eta)-2,4-di-1-pyrrolidino-2,4-cyclopentadien-1-yl]-N,N-bis(1-methylethyl)boranediaminato(2-)-kappaN'][(2,3,4,5-eta)-2,4-hexadiene]-titanium(II) and dimethyl[N'-(1,1-dimethylethyl)-1-[(1,2,3,4,5-eta)-2,4-di-1-pyrrolidino-2,4-cyclopenta-dien-1-yl]-N,N-bis(1-methylethyl)boranediaminato(2-)-kappaN']-titanium.

The metal complexes can be prepared by use of well known synthetic, techniques. Optionally a reducing agent can be employed to produce the lower oxidation state complexes. Such a process is disclosed in U.S. Pat. No. 5,470,993. The reactions are conducted in a suitable noninterfering solvent at a temperature from −100 to 300° C., preferably from −78 to 150° C., most preferably from 0 to 50° C. By the term "reducing agent" herein is meant a metal or compound which, under reducing conditions causes the metal M, to be reduced from a higher to a lower oxidation state. Examples of suitable metal reducing agents are alkali metals, alkaline earth metals, aluminum and zinc, alloys of alkali metals or alkaline earth metals such as sodium/mercury amalgam and sodium/potassium alloy. Examples of suitable reducing agent compounds are sodium naphthalenide, potassium graphite, lithium alkyls, lithium or potassium alkadienyls; and Grignard reagents. Most preferred reducing agents are the alkali metals or alkaline earth metals, especially lithium and magnesium metal.

Suitable reaction media for the formation of the complexes include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, and xylene, $C_{1-4}$ dialkyl ethers, $C_{1-4}$ dialkyl ether derivatives of (poly)alkylene glycols, and tetrahydrofuran. Mixtures of the foregoing are also suitable.

The synthesis of the bis(N,N-dihydrocarbylamino) cyclopentadienes of the invention is illustrated by the following schematic drawing:

wherein $R^A$, $R^B$, $R^C$, and Z are as previously defined.

Step a) may be performed by condensation of a secondary amine with the ketone according to the technique of W. E. Noland, V. Kameswaran *J. Org. Chem.* 1981, 46, 1940–1944. An acid catalyst such as p-toluene sulfonic acid may be employed, and the water by-product is desirably azeotropically removed using a benzene or toluene solvent under reflux conditions. Thereafter the amino-substituted cyclopenteneone is reacted with at least one-half equivalent of a titanium tetraamide. Alternatively, the neutral bis(N,N-dihydrocarbylamino)-substituted cyclopentadiene may be prepared directly by contacting the diketone with at least one equivalent of titanium tetraamide in an inert diluent at a temperature from 25 to 150° C. With more sterically-hindered ketones, such as 1,2-diketones, or more volatile amines, such as dimethyl amine, it may be preferable to employ stronger dehydrating reagents such as titanium chloroamides, which may be generated in situ by condensing titanium tetrachloride and the amine. This technique has been previously disclosed in R. Carlson, A. Nulsson, *Acta Chemica Scandinavica,* B 38, 1984, 49–53.

Subsequent formation of the substituted ligand groups (steps b), c), and d)) and ultimately the metal complexes uses conventional organometallic synthetic procedures. The skilled artisan will appreciate that the neutral bis(N,N-dihydrocarbylamino)-substituted cyclopentadiene is readily obtained by substitution of a proton source for the metallation step, b).

Desirably, the bis(N,N-dihydrocarbylamino)-substituted cyclopentadienes and intermediates prepared by these routes must be highly pure and free of ketone starting reactants, Aldol by-products, and higher weight reaction products which typically accompany product formation. Desirably the intermediate products may be subjected to purification procedures such as chromatographic purification, distillation, recrystallization, or other suitable technique to produce the desired purity in the final product. Rapid distillation of the diamine is preferred to prevent thermal polymerization in the still at elevated temperature.

Conversion of the diamine to its corresponding anionic salt may be accomplished by reaction with an appropriate base of suitable strength in an appropriate noninterfering solvent. Under anaerobic, anhydrous conditions, the often solid anionic salt may be filtered, washed and dried in nearly quantitative yield.

The formation of ligands containing the —Z— functional group from the diaminocyclopentadienes may be accomplished by reaction of the cyclopentadienyl anion with an electrophile such as a halogenated secondary alkylamine or halogenated secondary silylamine to give the corresponding cyclopentadienyl alkylamine or cyclopentadienyl silylamine. Suitable halogenated secondary alkylamines or halogenated secondary silylamines include (t-butyl)(chlorodimethylsilyl)amine, (t-butyl)(chlorodimethylsilylmethyl)amine, (t-butyl)(bromomethyldimethylsilyl)amine, (t-butyl)(2-chloroethyl)amine, (chlorodimethylsilyl)(phenyl)amine, (adamantyl)(chlorodiphenylsilyl)amine, (chlorodimethylsilyl)(cyclohexyl)amine, (benzyl)(chlorodimethylsilyl)amine and (t-butyl)(chloromethylphenylsilyl)amine. The technique is based upon the anion alkylation method previously disclosed by WO 93/08199 and *Organometallics,*1996, 15(6), 1572–81. In a preferred embodiment, the lithio-derivative of the anionic salt is slowly added to a molar excess of (t-butyl)(chlorodimethylsilyl)amine in an ether solvent.

By the term "appropriate noninterfering solvent" is meant a solvent that doesn't interfere with the formation of, or react deleteriously with, the desired product. Such solvents suitable for the preparation of the anionic salts of the invention include, but are not limited to, aliphatic and aromatic hydrocarbons, particularly straight and branched chain hydrocarbons such as butane, pentane, hexane, heptane, octane, decane, and mixtures thereof; cyclic and alicyclic hydrocarbons such as cyclohexane, cycloheptane, methylcyclohexane, methylcycloheptane and mixtures thereof; aromatic and hydrocarbyl-substituted aromatic compounds such as benzene, toluene, xylene, ethylbenzene, diethylbenzene and mixtures thereof; ethers and cyclic ethers, particularly $C_{1-6}$ dialkyl ethers, such as diethyl ether, dibutyl ether and methyl-t-butyl ether, $C_{1-6}$ dialkyl ether derivatives of (poly)alkylene glycols, such as dimethoxyethane, dioxane, tetrahydrofuran, and mixtures thereof. Mixtures of all of the foregoing solvents are also suitable.

Bases of suitable strength for the preparation of the dianionic salts of the invention include hydrocarbyl salts of Group 1 and Group 2 metals, especially alkyl or aryl salts of lithium or magnesium, such as methyllithium, ethyllithium, n-butyllithium, s-butyllithium, t-butyllithium, phenyllithium, methyl magnesium chloride, ethyl magnesium bromide, i-propyl magnesium chloride, dibutylmagnesium, (butyl)(ethyl)magnesium, dihexylmagnesium; Group 1 or Group 2 metals, such as lithium, sodium, potassium and magnesium; Group 1, Group 2 or Group 13 metal hydrides, such as lithium hydride, sodium hydride, potassium hydride or lithium aluminum hydride; Group 1 or Group 2 metal amide complexes, such as lithium diisopropylamide, lithium dimethylamide, lithium hexamethyldisilazide, sodamide and magnesium diisopropylamide.

Bases of suitable strength for the preparation of the anionic salts of the invention include the foregoing as well as Group 1 or Group 2 metal alkoxide complexes, such as sodium ethoxide, sodium t-butoxide, potassium butoxide and potassium amylate.

The metallation of the dianionic salt may be accomplished by methods cited in this art as well. Reaction of the dianionic salt with $TiCl_3$ $(THF)_3$, followed by oxidation with methylene chloride or lead dichloride, substantially according to the technique of *Chem. Ber.,* 1996, 129, 1429–1431 or EP-A-514,828 affords the titanium (IV) dichloride complex in very high yield. The dichloride may thereafter be silylated or hydrocarbylated by ligand exchange with an appropriate silylating or hydrocarbylating agent, such as methyllithium, methylmagnesiumchloride, benzylpotassium, allyllithium, trimethylsilylmethyllithium, neopentylmagnesiumbromide and phenyllithium.

A general method for producing the titanium(II) diene complex from the corresponding titanium(IV) dichloride preferably involves the treatment of the dichloride with n-butyllithium in the presence of an appropriate diene. A similar technique has been described in *Organometallics,* 1995, 14, 3132–3134 as well as in U.S. Pat. No. 5,556,928.

The formation of the metal complexes wherein the metal is in the +3 formal oxidation state according to the invention can be accomplished by any of several synthesis methods. One technique involves the reaction under anaerobic and anhydrous conditions of the dianionic salts with trivalent metal salts, such as Group 4 metal (III) halide or alkoxide complexes, optionally followed by silylation or hydrocarbylation with suitable silylating or hydrocarbylating agents, to form the corresponding halide, alkoxide, silyl or hydrocarbyl complexes of the invention. A further synthesis method involves reducing an appropriate metal (IV) complex with a suitable reducing agent to the corresponding metal (III) complex. Suitable reducing agents especially include zinc, aluminum and magnesium.

Suitable silylating and hydrocarbylating agents for the metal complexes of the invention include the corresponding silyl or hydrocarbyl derivatives of Group 1, 2 or 13 metals or Group 2 metal halides, preferably lithium sodium, potassium, magnesium and aluminum, or Group 2 metal Grignards. Examples of suitable hydrocarbyl and silyl groups include alkyl, such as methyl, ethyl, propyl, butyl, neopentyl and hexyl; aryl, such as phenyl, naphthyl and biphenyl; aralkyl, such as benzyl, tolylmethyl, diphenylmethyl; alkaryl, such as tolyl and xylyl; allyl; silyl- or alkyl-substituted allyl, such as methylallyl, trimethylsilylallyl, dimethylallyl and trimethylallyl; trialkylsilyl, such as trimethylsilyl and triethylsilyl; trialkylsilylalkyl, such as trimethylsilylmethyl; pentadienyl; alkyl- or silyl-substituted pentadienyl, such as methylpentadienyl, dimethylpentadienyl, trimethylsilylpentadienyl, bis (trimethylsilyl)pentadienyl, cyclohexadienyl and dimethylcyclohexadienyl; dialkylaminoalkaryl, such as o-(N,N-dimethylaminomethyl)phenyl; and dialkylaminoaralkyl, such as o-(N,N-dimethylamino)benzyl. Preferred silylating and hydrocarbylating agents include trimethylaluminum, methyllithium, methylmagnesiumchloride, neopentyllithium, trimethylsilylmethylmagnesiumchloride and phenyllithium. Stabilizing group-containing hydrocarbylating agents are also included, especially the stabilizing group-containing hydrocarbylating agents and salts of the stabilizing group-containing hydrocarbyl groups described in U.S. Pat. No. 5,504,224, whose salts include, for example, benzyl potassium, 2-(N,N-dimethylamino)benzyllithium, allyllithium and dimethylpentadienyl potassium. Such stabilizing groups are further described in U.S. Pat. No. 5,374,696, and elsewhere.

Preferred halides or alkoxides of the metal (III) halide or alkoxide complexes and the CGC metal (III) halide or alkoxide complexes include fluoride, chloride, bromide, iodide, methoxide, ethoxide, i-propoxide, n-propoxide, butoxide and phenoxide. Preferred metal (III) halide or alkoxide complexes include titanium (III) chloride, titanium (III) ethoxide, titanium (III) bromide, titanium (III) isopropoxide, titanium (III) (dichloro)(isopropoxide), as well as Lewis base complexes of the foregoing, especially ether complexes thereof, particularly diethylether, tetrahydrofuran and ethyleneglycol dimethyl ether complexes thereof. Preferred cyclopentadienyl-containing Group 4 metal complexes in the +3 oxidation state include triscyclopentadienyl titanium, biscyclopentadienyl titanium chloride, biscyclopentadienyl titanium bromide, biscyclopentadienyl titanium isopropoxide, cyclopentadienyl titanium dichloride, cyclopentadienyl titanium diphenoxide, cyclopentadienyl titanium dimethoxide and bis((trimethylsilyl)(t-butyl)cyclopentadienyl)zirconium chloride.

The invention further comprises certain bis(N,N-dihydrocarbylamino)-substituted cyclopentadiene compounds and ligands derived there from in the form of:

(A) a free base with 2 protons capable of being deprotonated;

(B) a dilithium or diGrignard salt;

(C) a magnesium salt; or (D) a monosilylated or a disilylated dianion.

Within the scope of this invention is the use of the foregoing ligand in a synthesis to produce a metal complex of this invention, for synthesis to produce a metal complex comprising a metal from one of Groups 3 to 13 of the Periodic Table of the Elements, the lanthanides or actinides, and from 1 to 4 of the foregoing ligands.

The ligands of this invention may be used in various forms, including salts, with various Z groups in syntheses leading to metal complexes containing from one to four such ligands, alone or in combination with other ligands using the foregoing syntheses or other synthetic procedures known in the art. The metal complexes are useful as catalysts in various reactions, including olefin polymerization reactions.

The structural representations of compounds and ligands utilized herein should not be given a strictly literal interpretation with regard to bond orders, bond lengths or strengths. In particular, the N-Cp bonds of some complexes herein may be shorter than would be expected for a single bond, thereby indicating the existence of at least some double bond character in the N-Cp bond of the present ligands, compounds and complexes, without departing from the scope of the present invention.

The complexes are rendered catalytically active by combination with an activating cocatalyst or by use of an activating technique. Suitable activating cocatalysts for use herein include polymeric or oligomeric alumoxanes, especially methylalumoxane, triisobutyl aluminum modified methylalumoxane, or isobutylalumoxane; neutral Lewis acids, such as $C_{1-45}$ hydrocarbyl substituted Group 13 compounds, especially tri(hydrocarbyl)aluminum- or tri (hydrocarbyl)boron compounds and halogenated (including perhalogenated) derivatives thereof, having from 1 to 15 carbons in each hydrocarbyl or halogenated hydrocarbyl group, more especially perfluorinated tri(aryl)boron compounds, and most especially tris(o-nonafluorobiphenyl) borane, tris(pentafluorophenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium salts of compatible, noncoordinating anions; bulk electrolysis (explained in more detail hereinafter); and combinations of the foregoing activating cocatalysts and techniques. The foregoing activating cocatalysts and activating techniques have been previously taught with respect to different metal complexes in EP-A-277,003 and U.S. Pat. Nos. 5,153,157, 5,064,802, 5,321,106, and 5,721,185.

Combinations of neutral Lewis acids, especially the combination of a trialkyl aluminum compound having from 1 to 4 carbons in each alkyl group and a halogenated tri (hydrocarbyl)boron compound having from 1 to 20 carbons in each hydrocarbyl group, especially tris (pentafluorophenyl)borane, tris(o-nonafluorobiphenyl) borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts. A benefit according to the present invention is the discovery that the most efficient catalyst activation using such a combination of tris(pentafluorophenyl)borane/ alumoxane mixture occurs at reduced levels of alumoxane. Preferred molar ratios of metal complex: tris (pentafluorophenyl)borane: alumoxane are from 1:1:1 to 1:5:5, more preferably from 1:1:1.5 to 1:5;3. The surprising efficient use of lower levels of alumoxane with the present invention allows for the production of olefin polymers with high catalytic efficiencies using less of the expensive alumoxane cocatalyst. Additionally, polymers with lower levels of aluminum residue, and hence greater clarity, are obtained.

Suitable ion forming compounds useful as cocatalysts in one embodiment of the present invention comprise a cation which is a Bronsted acid capable of donating a proton, and a compatible, noncoordinating anion, $A^-$. As used herein, the term "noncoordinating" means an anion or substance which either does not coordinate to the metal complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

$(L^*—H)^+_d(A)^{d-}$ wherein:

L* is a neutral Lewis base;

(L*—H)$^+$ is a Bronsted acid;

(A)$^{d-}$ is a noncoordinating, compatible anion having a charge of d–, and d is an integer from 1 to 3.

More preferably (A)$^{d-}$ corresponds to the formula: [M'Q$_4$]$^-$;

wherein:

M' is boron or aluminum in the +3 formal oxidation state; and

Q independently each occurrence is selected from hydride, dialkylamido, halide, hydrocarbyl, hydrocarbyloxide, halosubstituted-hydrocarbyl, halosubstituted hydrocarbyloxy, and halo-substituted silylhydrocarbyl radicals (including perhalogenated hydrocarbyl- perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433.

In a more preferred embodiment, d is one, that is, the counter ion has a single negative charge and is A$^-$. Activating cocatalysts comprising boron which are particularly useful in the preparation of catalysts of this invention may be represented by the following general formula:

$(L^*—H)^+(BQ_4)^-$;

wherein:

L* is as previously defined;

B is boron in a formal oxidation state of 3; and

Q is a hydrocarbyl-, hydrocarbyloxy-, fluorinated hydrocarbyl-, fluorinated hydrocarbyloxy-, or fluorinated silylhydrocarbyl-group of up to 20 nonhydrogen atoms, with the proviso that in not more than one occasion is Q hydrocarbyl.

Most preferably, 0 is each occurrence a fluorinated aryl group, especially, a pentafluorophenyl group.

Illustrative, but not limiting, examples of ion forming compounds comprising proton donatable cations which may be used as activating cocatalysts in the preparation of the catalysts of this invention are tri-substituted ammonium salts such as:

trimethylammonium tetraphenylborate,
methyldioctadecylammonium tetraphenylborate,
triethylammonium tetraphenylborate,
tripropylammonium tetraphenylborate,
tri(n-butyl)ammonium tetraphenylborate,
methyltetradecyloctadecylammonium tetraphenylborate,
N,N-dimethylanilinium tetraphenylborate,
N,N-diethylanilinium tetraphenylborate,
N,N-dimethyl(2,4,6-trimethylanilinium)tetraphenylborate,
trimethylammonium tetrakis(penta-fluorophenyl)borate,
triethylammonium tetrakis(pentafluorophenyl)borate,
triropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-diethylanilinium tetrakis(pentafluorophenyl)borate,
N,N-dimethyl(2,4,6-trimethylanilinium)tetrakis (pentafluorophenyl)borate,
trimethylammonium tetrakis(2,3,4,6-tetrafluorophenyl) borate,
triethylammonium tetrakis(2,3,4,6-tetrafluorophenyl)borate,
triropylammonium tetrakis(2,3,4,6-tetrafluorophenyl) borate,
tri(n-butyl)ammonium tetrakis(2,3,4,6-tetrafluorophenyl) borate,
dimethyl(t-butyl)ammonium tetrakis(2,3,4,6-tetrafluorophenyl)borate,
N,N-dimethylanilinium tetrakis(2,3,4,6-tetrafluorophenyl) borate,
N,N-diethylanilinium tetrakis(2,3,4,6-tetrafluorophenyl) borate, and
N,N-dimethyl-(2,4,6-trimethylanilinium)tetrakis-(2,3,4,6-tetrafluorophenyl)borate.

Dialkyl ammonium salts such as:

di-(i-propyl)ammonium tetrakis(pentafluorophenyl)borate, and
dicyclohexylammonium tetrakis(pentafluorophenyl)borate.

Tri-substituted phosphonium salts such as:

triphenylphosphonium tetrakis(pentafluorophenyl)borate,
tri(o-tolyl)phosphonium tetrakis(pentafluorophenyl)borate, and
tri(2,6-dimethylphenyl)phosphonium tetrakis (pentafluorophenyl)borate.

Preferred are tetrakis(pentafluorophenyl)borate salts of long chain alkyl mono- and disubstituted ammonium complexes, especially C$_{14}$–C$_{20}$ alkyl ammonium complexes, especially methyldi(octadecyl)ammonium tetrakis (pentafluorophenyl)borate and methyldi(tetradecyl) ammonium tetrakis(pentafluorophenyl)borate.

Especially preferred activating cocatalysts are tris (pentafluorophenyl)borane, (R$^1_2$NHCH$_3$)$^+$(C$_6$H$_4$OH)B (C$_6$F$_5$)$_3^-$, (R$^1_2$NHCH$_3$)$^+$B(C$_6$F$_5$)$_4^-$, or [(C$_6$H$_5$)NHR$^2_2$]$^+$B (C$_6$F$_5$)$_4^-$, where R$^1$ independently each occurrence is a substituted or unsubstituted saturated hydrocarbyl group having from 12 to 30 carbon atoms, and R$^2$ independently each occurrence is a substituted or unsubstituted saturated hydrocarbyl group having from 1 to 8 carbon atoms.

Another suitable ion forming, activating cocatalyst comprises certain imidazolide, substituted imidazolide, imidazolinide, substituted imidazolinide, benzimidazolide, or substituted benzimidazolide anions depicted schematically as follows:

wherein:

A** is a monovalent cation, preferably a trihydrocarbyl ammonium cation, containing one or two $C_{10-40}$ alkyl groups, especially the methylbis(tetradecyl)ammonium- or methylbis(octadecyl)ammonium-cation, $R^3$, independently each occurrence, is hydrogen or a halo, hydrocarbyl, halocarbyl, halohydrocarbyl, silylhydrocarbyl, or silyl, (including mono-, di- and tri(hydrocarbyl)silyl) group of up to 30 atoms not counting hydrogen, preferably $C_{1-20}$ alkyl, and J*' is tris(pentafluorophenyl)borane or tris(pentafluorophenyl)alumane).

Another suitable ion forming, activating cocatalyst comprises a salt of a cationic oxidizing agent and a noncoordinating, compatible anion represented by the formula:

$$(Ox^{e+})_d(A^{d-})_e$$

wherein:

$Ox^{e+}$ is a cationic oxidizing agent having a charge of e+;
e is an integer from 1 to 3; and
$A^{d-}$ and d are as previously defined.

Examples of cationic oxidizing agents include: ferrocenium, hydrocarbyl-substituted ferrocenium, $Ag^+$ and $Pb^{+2}$. Preferred embodiments of $A^{d-}$ are those anions previously defined with respect to the Bronsted acid containing activating cocatalysts, especially tetrakis(pentafluorophenyl)borate.

Another suitable ion forming, activating cocatalyst comprises a compound which is a salt of a carbenium ion and a noncoordinating, compatible anion represented by the formula:

wherein:

©⁺ is a $C_{1-20}$ carbenium ion; and
$A^-$ is as previously defined. A preferred carbenium ion is the trityl cation, that is, triphenylmethylium.

A further suitable ion forming, activating cocatalyst comprises a, compound which is a salt of a silylium ion and a noncoordinating, compatible anion represented by the formula:

$$R_3Si^+A^-$$

wherein:

R is $C_{1-10}$ hydrocarbyl, and $A^-$ are as previously defined.

Preferred silylium salt activating cocatalysts are trimethylsilylium tetrakispentafluorophenylborate, triethylsilylium tetrakispentafluorophenylborate and ether substituted adducts thereof. Silylium salts have been previously generically disclosed in *J. Chem Soc. Chem. Comm.*, 1993, 383–384, as well as Lambert, J. B., et al., *Organometallics*, 1994, 13, 2430–2443. The use of the above silylium salts as activating cocatalysts for addition polymerization catalysts is disclosed in U.S. Pat. No. 5,625,087.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433.

The technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are: liquids under the conditions of the electrolysis (generally temperatures from 0 to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), dimethoxyethane (DME), and mixtures thereof.

The electrolysis may be conducted in a standard electrolytic cell containing an anode and cathode (also referred to as the working electrode and counter electrode respectively). Suitable materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected. Suitable supporting electrolytes are salts comprising a cation and a compatible, noncoordinating anion, $A^-$.

Preferred supporting electrolytes are salts corresponding to the formula $G^+A^-$; wherein:

$G^+$ is a cation which is nonreactive towards the starting and resulting complex, and $A^-$ is as previously defined.

Examples of cations, $G^+$, include tetrahydrocarbyl substituted ammonium or phosphonium cations having up to 40 nonhydrogen atoms. Preferred cations are the tetra(n-butylammonium)- and tetraethylammonium-cations.

During activation of the complexes of the present invention by bulk electrolysis the cation of the supporting electrolyte passes to the counter electrode and $A^-$ migrates to the working electrode to become the anion of the resulting oxidized product. Either the solvent or the cation of the supporting electrolyte is reduced at the counter electrode in equal molar quantity with the amount of oxidized metal complex formed at the working electrode. Preferred supporting electrolytes are tetrahydrocarbylammonium salts of tetrakis(perfluoroaryl)borates having from 1 to 10 carbons in each hydrocarbyl or perfluoroaryl group, especially tetra(n-butylammonium)tetrakis-(pentafluorophenyl)borate.

A further recently discovered electrochemical technique for generation of activating cocatalysts is the electrolysis of a disilane compound in the presence of a source of a noncoordinating compatible anion. This technique is more fully disclosed in U.S. Pat. No. 5,372,682.

The foregoing electrochemical activating technique and activating cocatalysts may also be used in combination. An especially preferred combination is a mixture of a tri(hydrocarbyl)aluminum or tri(hydrocarbyl)borane compound having from 1 to 4 carbons in each hydrocarbyl group with an oligomeric or polymeric alumoxane compound.

The molar ratio of catalyst/cocatalyst employed preferably ranges from 1:10,000 to 100:1, more preferably from 1:5000 to 10:1, most preferably from 1:1000 to 1:1. Alumoxane, when used by itself as an activating cocatalyst, is employed in large quantity, generally at least 100 times the quantity of metal complex on a molar basis. Tris(pentafluorophenyl)borane, where used as an activating cocatalyst, is employed in a molar ratio to the metal complex of form 0.5:1 to 10:1, more preferably from 1:1 to 6:1, most preferably from 1:1 to 5:1. The remaining activating cocatalysts are generally employed in approximately equimolar quantity with the metal complex.

Suitable polymerizable monomers include ethylenically unsaturated monomers, acetylenic compounds, conjugated or non-conjugated dienes, and polyenes. Preferred monomers include olefins, for examples alpha-olefins having from 2 to 20,000, preferably from 2 to 20, more preferably from 2 to 8 carbon atoms and combinations of two or more of such alpha-olefins. Particularly suitable alpha-olefins include, for example, ethylene, propylene, 1-butene, 1-pentene, 4-methylpentene-1, 1-hexene, 1-heptene, 1-octene, 1-nonene, 1-decene, 1-undecene, 1-dodecene, 1-tridecene, 1-tetradecene, 1-pentadecene, or combinations thereof, as well as long chain vinyl terminated oligomeric or polymeric reaction products formed during the polymerization, and $C_{10-30}$ α-olefins specifically added to the reaction mixture in order to produce relatively long chain branches in the resulting polymers. Preferably, the alpha-olefins are ethylene, propene, 1-butene, 4-methyl-pentene-1, 1-hexene, 1-octene, and combinations of ethylene and/or propene with one or more of such other alpha-olefins. Other preferred monomers include styrene, halo- or alkyl substituted styrenes, tetrafluoroethylene, vinylcyclobutene, 1,4-hexadiene, dicyclopentadiene, ethylidene norbornene, and 1,7-octadiene. Mixtures of the above-mentioned monomers may also be employed.

In general, the polymerization may be accomplished at conditions well known in the prior art for solution phase, slurry, gas phase and high pressure Ziegler-Natta or Kaminsky-Sinn type polymerization reactions. Examples of such well known polymerization processes are depicted in U.S. Pat. Nos. 5,084,534, 5,405,922, 4,588,790, 5,032,652, 4,543,399, 4,564,647, 4,522,987, and elsewhere. Preferred polymerization temperatures are from 0–250° C. Preferred polymerization pressures are from atmospheric to 3000 atmospheres. Molecular weight control agents can be used in combination with the present cocatalysts. Examples of such molecular weight control agents include hydrogen, silanes or other known chain transfer agents. The catalyst composition may be used by itself (homogeneously) or supported on an inert support such as silica, alumina or a polymer.

The skilled artisan will appreciate that the invention disclosed herein may be practiced in the absence of any component which has not been specifically disclosed. The following examples are provided as further illustration of the invention and are not to be construed as limiting. Unless stated to the contrary all parts and percentages are expressed on a weight basis. Where stated, the term "room temperature" refers to a temperature from 20 to 25° C., the term "overnight" refers to a time from 12 to 18 hours, and the term "mixed alkanes" refers to a mixture of propylene oligomers sold by Exxon Chemicals Inc. under the trade designation Isopar™ E.

$^1H$ and $^{13}C$ NMR spectra were recorded on a Varian XL (300 MHz) spectrometer. Chemical shifts were determined relative to TMS or through the residual $CHCl_3$ in $CDCl_3$ or the residual $C_6HD_5$ in $C_6D_6$, relative to TMS. Tetrahydrofuran (THF), diethylether, toluene, and hexane were used following passage through double columns charged with activated alumina and alumina supported mixed metal oxide catalyst (Q-5® catalyst, available from Engelhard Corp.). The compounds n-BuLi, Grignard reagents were all used as purchased from Aldrich Chemical Company. All syntheses were performed under dry nitrogen atmosphere using a combination of glove box and high vacuum techniques.

EXAMPLE 1

Preparation of 1-(N,N-dimethylamino)-2-methyl-3-pyrrolidino-cyclopentadiene

2-Methyl-3-(1-pyrrolidino)-cyclopenten-1-one (2.00 g, 12.1 mmol) was dissolved in 40 mL of toluene. To this solution 1.55 mL (6.66 mmol) of $Ti(NMe_2)_4$ was added. After addition of titanium reagent copious amount of precipitate appeared but dissolved within 3 min. The reaction mixture assumed a deep red color. After an additional 10 min. a large amount of solid formed. Stirring of the reaction mixture was continued for 1 hour, after which the solvent was removed under reduced pressure. The residue was dissolved in 30 mL of hexane. Filtration and hexane removal gave 1.70 g, 73 percent of the desired product as an orange-red liquid which solidified on standing.

EXAMPLE 2

Preparation of 1,3-bis(N,N-dimethylamino)-2-methyl-1,3-cyclopentadiene

To a suspension of 4.0 g (35.67 mmol) of 2-methyl-1,3-cyclopentadione in 60 mL of toluene was added 8.75 mL (37.46 mmol) of $Ti(NMe_2)_4$. The reaction mixture darkened within few minutes to a dark red color. After stirring overnight, the solvent was removed under reduced pressure and the residue was extracted with 70 mL of hexane. Hexane was removed under reduced pressure leaving 2.72 g of a red oil. The residue was washed with 40 mL of toluene, filtered giving red solution. Toluene was removed under vacuum leaving 0.96 g of red oil. The product was identified as 1,3bis(N,N-dimethylamino)-2-methyl-1,3-cyclopentadiene by $^1$H and $^{13}$C NMR. Yield was 62 percent.

EXAMPLE 3

Preparation of 1,3-bis(N,N-dimethylamino)-1,3-cyclopentadiene

To a suspension of 2.0 g (20.37 mmol) of 1,3-cyclopentadione in 60 mL of toluene was added 5 mL (21.4 mmol) of Ti(NMe$_2$)$_4$. After stirring for 2 hours, 2 g more of 1,3-cyclopentadione was added followed by an additional 5 mL of Ti(NMe$_2$)$_4$. The reaction mixture was stirred overnight and then filtered through a medium frit. Solvent was removed under reduced pressure to give 3.70 g of the desired product as a red-oil. Proton and carbon NMR shows the presence of small quantities of dimethylamine containing products as well. These impurities can be removed by treating the solution of the product with excess of dry acetone, removing the resulting insolubles, followed by solvent removal leads to formation of pure 1,3-bis(N,N-dimethylamino)-1,3-cyclopentadiene product.

EXAMPLE 4

Preparation of 1,3-dipyrrolidino-1,3-cyclopentadiene

A mixture of 38.5 g (171.71 mmol) of Ti(NMe$_2$)$_4$ and 71.7 mL (858.7 mmol) of pyrrolidine in 200 mL of toluene was refluxed under N$_2$ overnight. Initial yellow color of the solution changed to yellow green. Toluene was removed under reduced pressure to give 55.22 g of tetrapyrrolidino titanium, Ti(NC$_4$H$_8$)$_4$, as a yellow green thick liquid. Yield was 97.9 percent.

To 2.245 g (14.85 mmol) of 3-(pyrrolidino)-2-cyclopenten-1-one dissolved in 50 mL of toluene was added 2.5 g (7.61 mmol) of the tetrapyrrolidino titanium. The reaction mixture became red with concomitant appearance of precipitate. The reaction mixture was stirred overnight and then filtered giving a dark red solution. Toluene was removed under reduced pressure to give 2.75 g of red crystalline solid. Yield was 90.6 percent. This product was then recrystallized from 60 mL of hexane to give 1.56 g of the desired product as large red-orange crystals.

EXAMPLE 5

Preparation of [(1,2,3,4,5-eta)-1,3-bis(N,N-dimethylamino)-2-methyl-2,4-cyclopentadien-1-yl]-lithium 1-(N,N-dimethylamino)-4-(pyrrolidino)-5-methyl-1,4-cyclopentadiene (1.00 g, 5.2 mmol), was dissolved in 30 mL of hexane. To this solution 3.25 mL of 1.6 M n-BuLi solution in hexane was added at room temperature. The color changed from orange to light yellow-white. After a few minutes the solution became too viscous to stir. An additional 30 mL quantity of hexane was added. After several minutes, white-pink, crystalline material started to appear and the solution became an easy flowing liquid again. After stirring for 3 hours, the solid was collected on a frit, washed with hexane and dried under reduced pressure to give 0.86 g of the desired product. Yield was 83 percent.

EXAMPLE 6

Preparation of [(1,2,3,4,5-eta)-1,3-bis(N,N-dimethylamino)-2-methyl-2,4-cyclopentadien-1-yl]-lithium 1,3-bis(N,N-dimethylamino)-2-methyl-1,3-cyclopentadiene, 6-A, (2.72 g, 16.4 mmol), was dissolved in 45 mL of hexane. To this solution 12.27 mL (19.6 mmol) of 1.6 M n-BuLi (in hexane) was added. During the addition a gray solid precipitated. After stirring for 4 hours, the solid was filtered, washed with hexane and dried under reduced pressure to give 2.76 g of [(1,2,3,4,5-eta)-1,3-bis(N,N-dimethylamino)-2-methyl-2,4-cyclopentadien-1-yl]-lithium, 6-B, as a white-gray solid. Yield was 98 percent.

EXAMPLE 7

Preparation of (N-t-butylamino)(dimethyl)(2-methyl-1,3-bis(dimethylamino)cyclopentadienyl) silane and dilithium salt

A solution of 1[(1,2,3,4,5-eta)-1,3-bis(N,N-dimethylamino)-2-methyl-2,4-cyclopentadien-1-yl]- lithium, 7-A, (1.6 g, 9.29 mmol) in 30 mL of tetrahydrofuran (THF) was added over 3 minutes at room temperature to 2.00 g (12.1 mmol) of ClSiMe$_2$-NH-t-Bu dissolved in 30 mL of THF. The resulting dark brown solution was stirred overnight. The solvent was removed under reduced pressure and the residue was extracted with hexane and filtered. Solvent was removed under reduced pressure leaving 2.72 g of 5-[[(1,1-dimethylethyl)amino]dimethylsilyl]-1,3-bis(N,N-dimethylamino)-2-methyl-1,3-cyclopentadiene 7-B, as a brown liquid. Approximate purity was 86 percent by GPC.

The neutral form of the silane 7-B (2.72 g, 9.2 mmol) was dissolved in 50 mL of hexane. To this solution 12.1 mL (19.33 mmol) of 1.6 M n-BuLi (in hexane) was added. During addition a gray solid precipitated. After stirring for 3 hours the solid was filtered, washed with hexane and dried under reduced pressure to give 2.81 g of [(1,2,3,4,5-eta)-1,3-bis(N,N-dimethylamino)-4-[[(1,1-dimethylethyl)amino]dimethylsilyl]-2-methyl-2,4-cyclopentadien-1-yl]-lithium, lithium salt as a gray solid. Yield was 99 percent.

EXAMPLE 8

Preparation of (N-t-butylamido)(dimethyl)(2-methyl-1,3-bis(N,N-dimethylamino)cyclopentadienyl)silanetitanium dichloride

In a drybox, 2.061 g (5.56 mmol) of TiCl$_3$(THF)$_3$ was suspended in 40 mL of THF. To this solution 1.71 g (5.56 mmol) of [(1,2,3,4,5-eta)-1,3-bis(dimethylamino)-4-[[(1,1-dimethylethyl)amino]dimethylsily]-2-methyl-2,4-cyclopentadien-1-yl]-lithium, lithium salt dissolved in 15 mL of THF was added within 2 min. The solution was then stirred for 55 min. After this time 1.006 g of PbCl$_2$ (3.62 mmol) was added and the solution was stirred for 2 hours resulting in a deep red-purple solution. The THF was then removed under reduced pressure. The residue was then extracted with 40 mL of toluene, the solution was filtered and the toluene was removed under reduced pressure. The residue was then dissolved in 50 mL of hexane and solution was filtered leaving some gray precipitate on the frit. Hexane solution was put aside into a freezer (−27° C.) overnight. The resulting black crystals were washed with hexane and then dried under reduced pressure to give 1.07 g of, [1-[(1,2,3,4,5-eta)-2,4-bis(N,N-dimethylamino)-3-methyl-2,4-cyclopentadien-1-yl]-N-(1,1-dimethylethyl)-1,1-dimethylsilanaminato(2-)-kappaN]titanium dichloride, 8-B. Yield was 46.7 percent.

$^1$H (C$_6$D$_6$) δ 0.39 (s, 3H), 0.49 (s, 3H), 1.47 (s, 9H), 2.08 (s, 3H), 2.67 (s, 6H), 2.72 (s, 6H), 5.43 (s, 1 H).

$^{13}$C{$^1$H}(C$_6$D$_6$) δ 1.48, 3.85, 14.31, 33.12, 42.24, 45.18, 61.44, 95.74, 107.73, 116.56, 153.74, 157.98.

EXAMPLE 9

Preparation of lithium 1,3-dipyrrolidinocyclopentadienide 1,1'-(1,3-cyclopentadiene-1,3-diyl)bis-Pyrrolidine (1.86 g, 9.08 mmol), 9-A, was dissolved in 50 mL of hexane. To this solution 6.53 mL (10.45 mmol) of 1.6 M n-BuLi (in hexane) was added. A white crystalline solid was formed after n-BuLi addition. After stirring the reaction mixture overnight the solid was filtered, washed with hexane and dried under reduced pressure to give 1.87 g of [(1,2,3,4,5-eta)-1-(dimethylamino)-2-methyl-3-(1-pyrrolidino-2,4-cyclopentadien-1-yl]-lithium 9-B, as a white solid. Yield was 98 percent.

EXAMPLE 10

Preparation of [(1,2,3,4,5-eta)-1-[[(1,1-dimethylethyl)amino]dimethylsilyl]-2,4-di-1-pyrrolidino)-2,4-cyclopentadien-1-yl]-lithium, lithium salt

[(1,2,3,4,5-eta)-1-(dimethylamino)-2-methyl-3-(1-pyrrolidino-2,4-cyclopentadien-1-yl]-lithium 10A, (1.00 g,

4.76 mmol) was added as a 20 mL THF suspension to a 30 mL THF solution of ClSiMe$_2$-NH-t-Bu. After 13 hours of mixing the originally formed precipitate dissolved and a homogenous (red color) solution was obtained. Solvent was removed under reduced pressure and the residue was extracted with 30 mL of hexane and filtered. Hexane was evaporated leaving 1.56 g of product as a red oil. Yield was 99 percent. Proton and Carbon NMR spectra show presence of N-(1,1-dimethylethyl)-1-(2,4-di-1-pyrrolidino-2,4-cyclopentadien-1-yl)-1,1-dimethyl-silanamine 10-B, as the predominant product.

N-(1,1-dimethylethyl)-1-(2,4-di-1-pyrrolidino-2,4-cyclopentadien-1-yl)-1,1-dimethyl-silanamine, 10-B, (1.52 g, 4.56 mmol) was dissolved in 50 mL of hexane. To this solution, 6.27 mL (10.0 mmol) of 1.6 M n-BuLi solution was added. During addition of the n-BuLi, the solution changed color from red to light yellow. Within a minute white crystalline precipitate appeared. The reaction mixture was stirred overnight and then the white solid was collected on a frit, washed with hexane and dried under reduced pressure to give 1.183 g of [(1,2,3,4,5-eta)-1-[[(1,1-dimethylethyl)amino]dimethylsilyl]-2,4-di-1-pyrrolidino)-2,4-cyclopentadien-1-yl]-lithium, lithium salt, 10-C. Yield was 75 percent.

EXAMPLE 11

Preparation of dichloro[N-(1,1-dimethylethyl)-1-[(1,2,3,4,5-eta)-2,4-di-1-pyrrolidino-2,4-cyclopentadien-1-yl]-1,1-dimethylsilanaminato(2-)-kappaN]-titanium -continued

11-B

In a drybox, 1.22 g (3.29 mmol) of TiCl$_3$(THF)$_3$ was suspended in 25 mL of THF. To this mixture a suspension of 1.137 g (3.29 mmol) of [(1,2,3,4,5-eta)-1-[[(1,1-dimethylethyl)amino]dimethylsilyl]-2,4-di-1-pyrrolidino)-2,4-cyclopentadien-1-yl]-lithium, lithium salt 11-A in 15 mL of THF was added within 2 min. The solution was then stirred for 55 min. The solution assumed a black-green color. After this time, 0.595 g of PbCl$_2$ (2.14 mmol) was added and the solution was stirred for 2 h resulting in a very dark green solution. The THF was then removed under reduced pressure. The residue was extracted with 40 mL of toluene, the solution was filtered, and the toluene was removed under reduced pressure. The residue was then dissolved in 50 mL of hexane and the solution was filtered. Solvent was removed leaving 1.152 g of dark green solid. Yield was 77.7 percent.

$^1$H (C$_6$D$_6$) δ 0.55 (s, 3H), 0.64 (s, 3H), 1.3–1.6 (m, 8H), 1.51 (s, 9H), 2.9–3.5 (very br. 4H), 2.97 (m, 2H), 3.42 (m, 2H), 5.27 (m, 2H).

$^{13}$C{$^1$H}(C$_6$D$_6$) δ (22° C.) 3.34, 5.10, 25.61, 25.79, 33.44, 48.33 (br.), 50.89, 60.55, 86.01, 89.83, 102.48, 152.26, 153.34.

Figure 1:
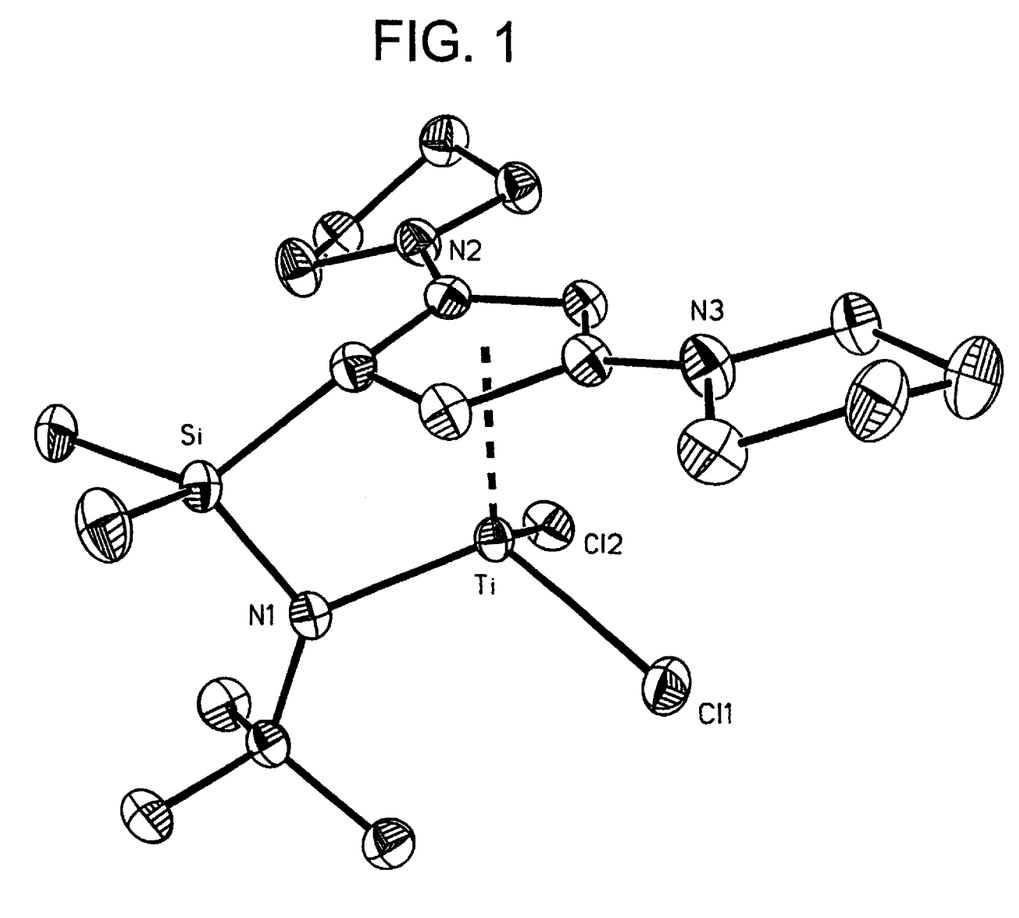
FIG. 1 is the ORTEP structure of compound 11b in example 11 as determined by X-ray crystal analysis.

The ORTEP structure of compound 11b, as determined from single crystal X-ray analysis is FIG. 1.

EXAMPLE 12

Preparation of [N-(1,1-dimethylethyl)-1-[(1,2,3,4,5-eta)-2,4-di-1-pyrrolidino-2,4-cyclopentadien-1-yl]-1,1-dimethylsilanaminato(2)-kappaN]dimethyl-titanium C$_{19}$H$_{33}$Cl$_2$N$_3$SiTi
Mol. Wt.: 450.3434

12 A

-continued

C₂₁H₃₉N₃SiTi
Mol. Wt.: 409.5071

12 B

Dichloro[N-(1,1-dimethylethyl)-1-[(1,2,3,4,5-eta)-2,4-di-1-pyrrolidino-2,4-cyclopentadien-1-yl]-1,1-dimethylsilanaminato(2-)-kappaN]-titanium, 12-A, (0.358 g, 0.79 mmol) was dissolved in 30 mL of ether. To this solution 0.56 mL (1.67 mmol) of MeMgI was added as a 3 M solution in ether. The reaction mixture changed color from black-greem to red. After stirring for 1.5 h at room temperature, solvent was removed under reduced pressure. The residue was extracted with 30 mL of hexane, filtered and dried under reduced pressure. This residue was again dissolved in 20 mL of hexane and filtered through fine frit. Hexane was removed leaving 0.292 g of red oil identified as 12-B. Yield was 89.7 percent.

EXAMPLE 13

Preparation of [1-[(1,2,3,4,5-eta)-2,4-bis(dimethylamino)-3-methyl-2,4-cyclopentadien-1-yl]-N-(1,1-dimethylethyl)-1,1-dimethylsilanaminato(2-)-kappaN]dimethyl-titanium C₁₆H₃₁Cl₂N₃SiTi
Mol. Wt.: 412.2955

13-A

2 MeMgI →

C₁₈H₃₇N₃SiTi
Mol. Wt.: 371.4591

13-B

[1-[(1,2,3,4,5-eta)-2,4-bis(N,N-dimethylamino)-3-methyl-2,4-cyclopentadien-1-yl]-N-(1,1-dimethylethyl)-1,1-dimethylsilanaminato(2-)-kappaN]dichloro-titanium, 13-A, (0.458 g, 1.11 mmol) was dissolved in 25 mL of ether. To this solution 0.74 mL (2.22 mmol) of MeMgI was added as 3 M solution in ether. The reaction mixture changed color from black-purple to red. After stirring for 35 min at room temp. solvent was removed under reduced pressure. The residue was extracted with 30 mL of hexane, filtered and dried under reduced pressure. This residue was again dissolved in 20 mL of hexane and filtered through a fine frit. Hexane was removed leaving 0.395 g of a red oil, identified as 13-B. Yield was 95.7 percent.

Polymerization

EXAMPLE 14

A two-liter Parr reactor was charged with 740 g of mixed alkanes solvent and 118 g of 1-octene comonomer. Hydrogen was added as a molecular weight control agent by differential pressure expansion from a 75 mL addition tank at 25 psi (2070 kPa). The reactor was heated to the polymerization temperature of 140° C. and saturated with ethylene at 500 psig (3.4 MPa). The appropriate amount of catalyst and cocatalyst as 0.005M solutions in toluene were premixed in the drybox. After the desired premix time, the solution was transferred to a catalyst addition tank and injected into the reactor. The polymerization conditions were maintained for 15 minutes with ethylene on demand. The resulting solution was removed from the reactor, and a hindered phenol antioxidant (Irganox™ 1010 from Ciba Geigy Corporation) was added to the resulting solution. Polymers formed were dried in a vacuum oven set at 120° C. for about 20 hours. Results are contained in Table 1.

TABLE 1

| Run | Catalyst[a] | Cocatalyst[b] | Efficiency[c] | MI[d] |
|---|---|---|---|---|
| 1* | 1 | B(C₆F₅)₃ | 787,000 | 10.2 |
| 2 | 2 | " | 320,000 | 0.8 |
| 3 | 3 | " | 802,000 | 2.5 |

*comparative, not an example of the invention
[a]. Catalyst 1. [N-(1,1-dimethyl)-1,1-dimethyl-1-[(1,2,3,4,5-η)-2,3,4,5-tetramethyl-2-4-cyclopentadien-1-yl]silanaminato(2-)-N]dimethyl-titanium (US-A-5,703,187)
Catalyst 2. [N-(1,1-dimethylethyl)-1-[(1,2,3,4,5-eta)-2,4,-di-1-pyrrolidino-2,4-cyclopentadien-1-yl]-1,1-dimethylsilanaminato(2-)-kappaN]dimethyl-titanium(example 12)
Catalyst 3. [1-[1,2,3,4,5-eta)-2,4-bis(N,N-dimethylamino-3-methyl-2,4-cyclopentadien-1-yl]-N-(1,1-dimethylethyl)-1,1-dimethylsilanaminato(2-)-kappaN]dimethyl-titanium (example 13)
[b]. Equimolar amounts of catalyst and cocatalyst were premixed together
[c]. grams polymer per gram TI
[d]. melt index (dg/min) determined by micromelt index method.

What is claimed is:
1. A metal complex corresponding to the formula:

III

IIIA

-continued wherein,

M is a metal from one of Groups 3 to 13 of the Periodic Table of the Elements, the lanthanides or actinides, which is in the +2, +3 or +4 formal oxidation state, $R^A$ independently each occurrence is hydrogen, hydrocarbyl, halo-substituted hydrocarbyl, hydrocarbyloxy-substituted hydrocarbyl, dihydrocarbylamino-substituted hydrocarbyl, hydrocarbadiylamino, hydrocarbylsilyl, hydrocarbylsilylhydrocarbyl, or one of the forgoing groups that is substituted with one or more hydrocarbyloxy, hydrocarbylsiloxy, hydrocarbylsilylamino, di(hydrocarbylsilyl)amino, hydrocarbadiylamino, di(hydrocarbyl)amino, di(hydrocarbyl)phosphino, hydrocarbylsulfido, hydrocarbyl, halo-substituted hydrocarbyl, hydrocarbyloxy-substituted hydrocarbyl, hydrocarbylamino-substituted hydrocarbyl, hydrocarbylsilyl or hydrocarbylsilylhydrocarbyl groups having from 1 to 20 nonhydrogen atoms;

$R^B$ and $R^C$ independently each occurrence are hydrocarbyl, hydrocarbylsilyl, halo-substituted hydrocarbyl, hydrocarbyloxy-substituted hydrocarbyl, di(hydrocarbyl)amino-substituted hydrocarbyl, hydrocarbylsilylhydrocarbyl, hydrocarbadiylamino, di(hydrocarbyl)amino, or hydrocarbyloxy, each $R^B$ and $R^C$ having from 1 to 80 atoms not counting hydrogen, and optionally being substituted with one or more groups which independently each occurrence are hydrocarbyloxy, hydrocarbylsiloxy, hydrocarbylsilylamino, di(hydrocarbylsilyl)amino, hydrocarbadiylamino, di(hydrocarbyl)amino, di(hydrocarbyl)phosphino, hydrocarbylsulfido, hydrocarbyl, hydrocarbylsilyl, hydrocarbylsilylhydrocarbyl, halo-substituted hydrocarbyl, hydrocarbyloxy-substituted hydrocarbyl, or hydrocarbylamino-substituted hydrocarbyl, said group having from 1 to 20 atoms not counting hydrogen, or two $R^B$ or two $R^C$ groups are covalently linked to form one or more fused rings;

Z is a divalent moiety comprising boron, or a member of Group 14 of the Periodic Table of the Elements, and also comprising nitrogen, phosphorus, sulfur or oxygen;

X is an anionic or dianionic ligand group having up to 60 atoms exclusive of the class of ligands that are cyclic, delocalized, π-bound ligand groups;

X' independently each occurrence is a neutral Lewis base ligand having up to 20 atoms;

p is zero, 1 or 2, and is two less than the formal oxidation state of M, when X is an anionic ligand; when X is a dianionic ligand group, p is 1; and q is zero, 1 or 2.

2. The metal complex of claim 1, wherein $R^B$ and $R^C$ are selected from the group consisting of hydrocarbyl, hydrocarbyloxy-substituted hydrocarbyl, and hydrocarbylamino-substituted hydrocarbyl radicals of 1–20 carbon atoms, or two $R^B$ or two $R^C$ groups combine to form a ring structure; and $R^A$ is hydrogen, a hydrocarbyl, halo-substituted hydrocarbyl, hydrocarbyloxy-substituted hydrocarbyl or hydrocarbylamino-substituted hydrocarbyl radical containing from 1–20 carbon atoms.

3. The metal complex of claim 2, wherein —Z— is —(Z*—Y)—, with Z* bonded to Cp and Y bonded to M, and

Y is —O—, —S—, —NR*—, or —PR*—;

Z* is $SiR^*_2$, $CR^*_2$, $SiR^*_2SiR^*_2$, $CR^*_2CR^*_2$, $CR^*=CR^*$, $CR^*_2SiR^*_2$, $CR^*_2SiR^*_2CR^*_2$, $SiR^*_2CR^*_2SiR^*_2$, $CR^*_2CR^*_2SiR^*_2$, $CR^*_2CR^*_2CR^*_2$, or $GeR^*_2$; and R* independently each occurrence is hydrogen, or a member selected from hydrocarbyl, hydrocarbyloxy, silyl, halogenated alkyl, halogenated aryl, and combinations thereof, said R* having up to 20 atoms not counting hydrogen, and optionally, two R* groups from Z* (when R* is not hydrogen), or an R* group from Z* and an R* group from Y form a ring system; where p is 0, q is 1, M is in the +2 formal oxidation state, and X' is 1,4-diphenyl-1,3-butadiene, 1,3-pentadiene or 2,4-hexadiene.

4. The metal complex of claim 3 wherein —N($R^B$)$_2$ and —N($R^C$)$_2$ are independently dimethylamino or pyrollidino and $R^A$ is either hydrogen or methyl, Z* is $SiR^*_2$ and Y is NR* and M is titanium or zirconium.

5. The metal complex of claim 4 corresponding to the formula:

wherein —N($R^B$)$_2$ and —N($R^C$)$_2$ are independently N,N-dimethylamino or pyrrolidino, $R^A$ independently each occurrence is methyl or hydrogen, M is titanium, and X is chloride or methyl.

6. The process of polymerizing at least one α-olefin comprising contacting such olefin with a catalyst derived from the complex of claim 4 by combination with an activating cocatalyst.

* * * * *